US00PP16110P2

(12) United States Plant Patent
Wain

(10) Patent No.: US PP16,110 P2
(45) Date of Patent: Nov. 8, 2005

(54) ***CHRYSANTHEMUM* PLANT NAMED 'YOTABITHA'**

(50) Latin Name: *Chrysanthemum×morifolium*
Varietal Denomination: Yotabitha

(75) Inventor: Peter Wain, Hants (GB)

(73) Assignee: Yoder Brothers, Inc., Barberton, OH (US)

( * ) Notice: Subject to any disclaimer, the term of this patent is extended or adjusted under 35 U.S.C. 154(b) by 17 days.

(21) Appl. No.: 10/937,783

(22) Filed: Sep. 8, 2004

(51) Int. Cl.[7] ..... A01H 5/00
(52) U.S. Cl. ..... Plt./293
(58) Field of Search ..... Plt./293

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Chrysanthemum* plant named 'Yotabitha', characterized by its upright, outwardly spreading and rounded plant habit; freely branching habit; freely flowering habit; decorative-type inflorescences with elongated oblong-shaped ray florets; red-colored ray florets; natural season flowering in late September in the Northern Hemisphere; and good garden performance.

2 Drawing Sheets

Botanical classification/cultivar designation: *Chrysanthemum×morifolium* cultivar Yotabitha.

BACKGROUND OF THE INVENTION

The present invention relates to a new and distinct cultivar of *Chrysanthemum* plant, botanically known as *Chrysanthemum×morifolium*, commercially known as a garden-type *Chrysanthemum* and hereinafter referred to by the name 'Yotabitha'.

The new cultivar is a product of a planned breeding program conducted by the Inventor in Fareham, Hants, United Kingdom. The objective of the breeding program is to create new garden-type *Chrysanthemum* cultivars having inflorescences with desirable inflorescence forms, attractive floret coloration and good garden performance.

The new *Chrysanthemum* originated from a cross-pollination made in March, 2001 in Fareham, Hants, United Kingdom of a proprietary *Chrysanthemum×morifolium* seedling selection identified as code number G114A 1, not patented, as the female, or seed, parent with a proprietary *Chrysanthemum×morifolium* seedling selection identified as code number G57A 1, not patented, as the male, or pollen, parent. The new *Chrysanthemum* was discovered and selected by the Inventor as a single flowering plant within the progeny of the stated cross-pollination grown in a controlled environment in Fareham, Hants, United Kingdom in September, 2001. The selection of this plant was based on its desirable inflorescence form, attractive floret coloration and good garden performance.

Asexual reproduction of the new cultivar by terminal vegetative cuttings in a controlled environment in Fareham, Hants, United Kingdom since December, 2001, has shown that the unique features of this new *Chrysanthemum* are stable and reproduced true to type in successive generations.

SUMMARY OF THE INVENTION

The cultivar Yotabitha has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yotabitha'. These characteristics in combination distinguish 'Yotabitha' as a new and distinct cultivar of *Chrysanthemum:*

1. Upright, outwardly spreading and rounded plant habit.
2. Freely branching habit.
3. Freely flowering habit.
4. Decorative-type inflorescences with elongated oblong-shaped ray florets.
5. Red-colored ray florets.
6. Natural season flowering in late September in the Northern Hemisphere.
7. Good garden performance.

In side-by-side comparisons conducted in Fareham, Hants, United Kingdom, plants of the new *Chrysanthemum* differed from plants of the female parent, the proprietary seedling selection identified as code number G114A 1, in the following characteristics:

1. Plants of the new *Chrysanthemum* were more rounded than plants of the female parent selection.
2. Plants of the new *Chrysanthemum* had smaller inflorescences and fewer disc florets per inflorescence than plants of the female parent selection.

In side-by-side comparisons conducted in Fareham, Hants, United Kingdom, plants of the new *Chrysanthemum* differed from plants of the male parent, the proprietary seedling selection identified as code number G57A 1, in the following characteristics:

1. Plants of the new *Chrysanthemum* were larger than plants of the male parent selection.
2. Plants of the new *Chrysanthemum* and the male parent selection differed in ray floret coloration as plants of the male parent selection had pink-colored ray florets.

Plants of the new *Chrysanthemum* can be compared to plants of the *Chrysanthemum* cultivar Bravo, disclosed in U.S. Plant Pat. No. 6,888. In side-by-side comparisons conducted in Alva, Fla. under natural season conditions, plants of the new *Chrysanthemum* differed from plants of the cultivar Bravo in the following characteristics:

1. Plants of the new *Chrysanthemum* were more rounded, fuller and more uniform in plant habit than plants of the cultivar Bravo.
2. Plants of the new *Chrysanthemum* flowered about one week later than plants of the cultivar Bravo.
3. Ray florets of plants of the new *Chrysanthemum* resisted fading better than ray florets of plants of the cultivar Bravo.

Plants of the new *Chrysanthemum* can also be compared to plants of the *Chrysanthemum* cultivar Jenny Wren, disclosed in U.S. Plant Pat. No. 10,213. In side-by-side comparisons conducted in Alva, Fla. under natural season conditions, plants of the new *Chrysanthemum* differed from plants of the cultivar Jenny Wren in the following characteristics:

1. Plants of the new *Chrysanthemum* were more rounded than but not as outwardly spreading as plants of the cultivar Jenny Wren.
2. Plants of the new *Chrysanthemum* had slightly smaller inflorescences than plants of the cultivar Jenny Wren.
3. Plants of the new *Chrysanthemum* flowered more uniformly than plants of the cultivar Jenny Wren.
4. Ray florets of plants of the new *Chrysanthemum* were darker red in color than ray florets of plants of the cultivar Jenny Wren.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph on the first sheet comprises a side perspective view of a typical flowering plant of 'Yotabitha' grown in a container.

The photograph on the second sheet comprises a close-up view of typical inflorescences of the cultivar 'Yotabitha'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Leamington, Ontario, Canada during the late summer and fall in an outdoor nursery and under conditions and practices which approximate those generally used in commercial garden-type *Chrysanthemum* production. One cutting was planted in a 15.25-cm container in mid-July. During the production of the plants, plants were exposed to natural season photoperiodic conditions with day temperatures averaging 26° C. and night averaging 18° C. Measurements and numerical values represent averages for typical flowering plants.

Botanical classification: *Chrysanthemum×morifolium* cultivar Yotabitha.

Commercial classification: Decorative-type garden *Chrysanthemum*.

Parentage:

*Female, or seed, parent.*—Proprietary *Chrysanthemum×morifolium* seedling selection identified as code number G114A 1, not patented.

*Male, or pollen, parent.*—Proprietary *Chrysanthemum×morifolium* seedling selection identified as code number G57A 1, not patented.

Propagation:

*Type.*—Terminal vegetative cuttings.

*Time to initiate roots, year-round.*—About four days at 21° C.

*Time to produce a rooted cutting, year-round.*—About ten to twelve days at 21° C.

*Root description.*—Fine, fibrous; white in color.

*Rooting habit.*—Freely branching.

Plant description:

*Plant form/growth habit.*—Perennial herbaceous decorative-type garden *Chrysanthemum*. Inverted triangle with rounded crown. Stems initially upright, then outwardly spreading. Freely branching with about twelve lateral branches per plant. Moderately vigorous.

*Plant height.*—About 17 cm.

*Plant diameter.*—About 27.5 cm.

*Lateral branches.*—Length: About 15 cm. Diameter: About 5.5 mm. Internode length: About 1.1 cm. Strength: Strong. Texture: Pubescent. Color: Closet to 146A.

*Foliage description.*—Leaf arrangement: Alternate. Length: About 4.5 cm. Width: About 3.5 cm. Apex: Mucronate. Base: Attenuate with truncate tendencies. Margin: Palmately and deeply lobed; sinuses mostly divergent. Texture, upper and lower surfaces: Pubescent. Color: Developing foliage, upper surface: Close to 147A. Developing foliage, lower surface: Lighter green than 147A. Fully expanded foliage, upper surface: More green than 147A. Fully expanded foliage, lower surface: Close to 147B. Venation, upper and lower surfaces: Close to 146A. Petiole: Length: About 1.7 cm. Diameter: About 3 mm. Texture, upper and lower surfaces: Pubescent. Color, upper and lower surfaces: Close to 146C.

Inflorescence description:

*Appearance.*—Decorative-type inflorescence form with elongated oblong-shaped ray florets. Inflorescences borne on terminals above foliage, arising from leaf axils. Disc and ray florets developing acropetally on a capitulum. Inflorescences face mostly upright or outwardly. Inflorescences hemispherical in shape. Freely flowering habit; about 15 inflorescences develop per lateral branch. Inflorescences persistent. Inflorescences not fragrant.

*Flowering response.*—Under natural season conditions, plants flower in late September in the Northern Hemisphere.

*Inflorescence bud (before showing color).*—Height: About 8 mm. Diameter: About 8.5 mm. Shape: Oblate to spherical. Color (lower surface of phyllaries): More green than 147A.

*Inflorescence size.*—Diameter: About 5 cm. Depth (height): About 2 cm. Disc diameter: About 3 mm. Receptacle diameter: About 5 mm. Receptacle height: About 5.5 mm.

*Ray florets.*—Shape: Elongated oblong. Length: About 2.4 cm. Corolla tube length: About 1.1 cm. Width: About 8 mm. Apex: Emarginate. Margin: Fused. Texture: Smooth, glabrous; satiny. Surface: Concave. Orientation: Initially upright, then perpendicular to the peduncle. Number of ray florets per inflorescence: About 224 in numerous whorls. Color:

When opening, upper and lower surfaces: Close to 59A. Fully opened, upper surface: Close to 154A to 10B overlain with close to 53A to 59A. Fully opened, lower surface: Close to 154A underlain with close to 187A.

*Disc florets.*—Shape: Tubular; apex dentate, five-pointed. Length: About 6 mm. Width, apex: About 1.5 mm. Width, base: About 1 mm. Number of disc florets per inflorescence: Very few, less than ten; inconspicuous. Color: Immature: Close to 154A. Mature: Apex: Close to 9A. Mid-section: Close to 154D. Base: More green than 155D.

*Phyllaries.*—Quantity per inflorescence: About 20. Length: About 1.1 cm. Width: About 4 mm. Shape: Deltoid, elongated. Apex: Acute. Base: Truncate, fused. Margin: Entire. Texture, upper surface: Smooth, waxy. Texture, lower surface: Pubescent. Color, upper surface: Close to 146A. Color, lower surface: More green than 147A.

*Peduncle.*—Length: First peduncle: About 5.5 cm. Fourth peduncle: About 9.2 cm. Seventh peduncle: About 11 cm. Diameter: About 3 mm. Strength: Strong. Aspect: About 45° from vertical. Texture: Pubescent. Color: Close to 146A.

*Reproductive organs.*—Androecium: Present on disc florets only. Anther color: Close to 9A. Pollen: None observed. Gynoecium: Present on both ray and disc florets.

*Seed/fruit.*—Seed and fruit production has not been observed.

Disease/pest resistance: Plants of the new *Chrysanthemum* have not been shown to be resistant to pathogens and pests common to *Chrysanthemums.*

Garden performance: Plants of the new *Chrysanthemum* have been observed to be have good garden performance and to be tolerant to rain, wind and temperatures ranging from 0 to greater than 38° C.

It is claimed:

1. A new and distinct cultivar of *Chrysanthemum* plant named 'Yotabitha', as illustrated and described.

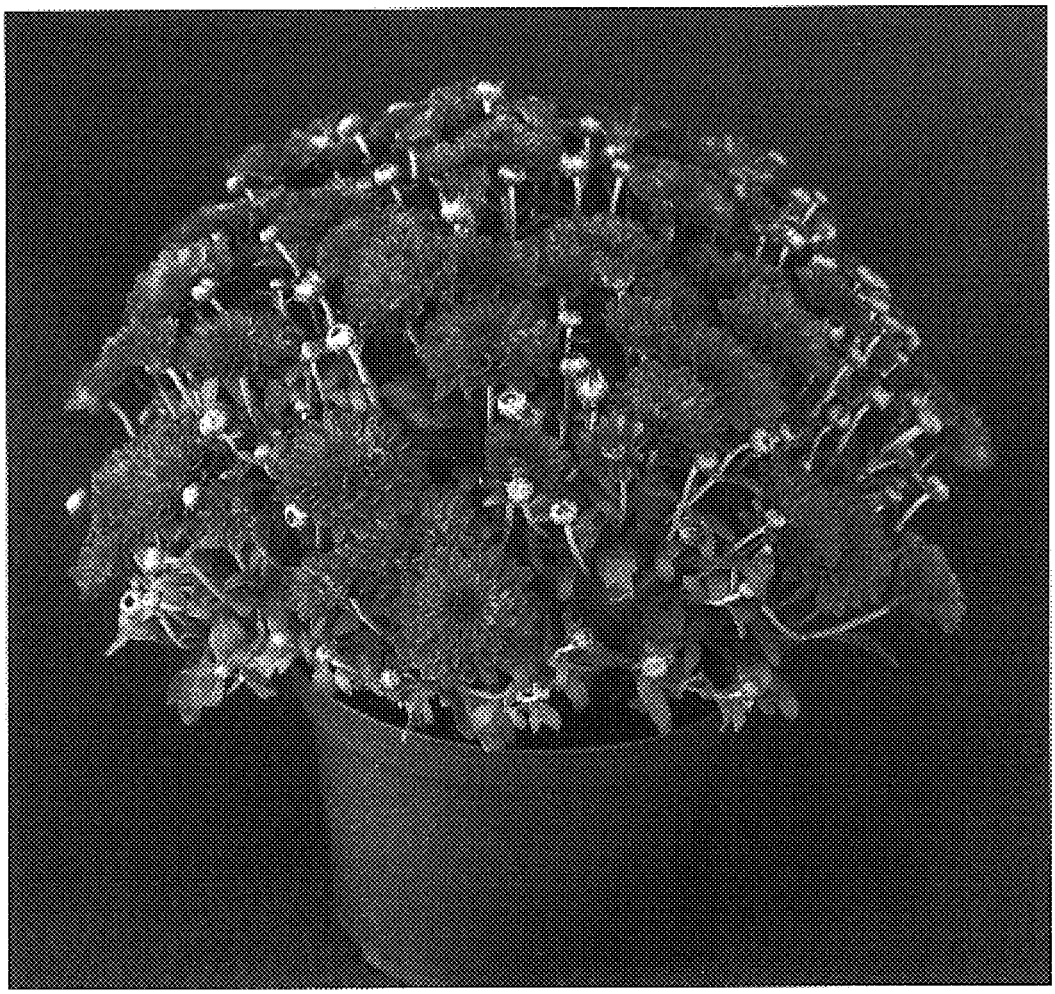

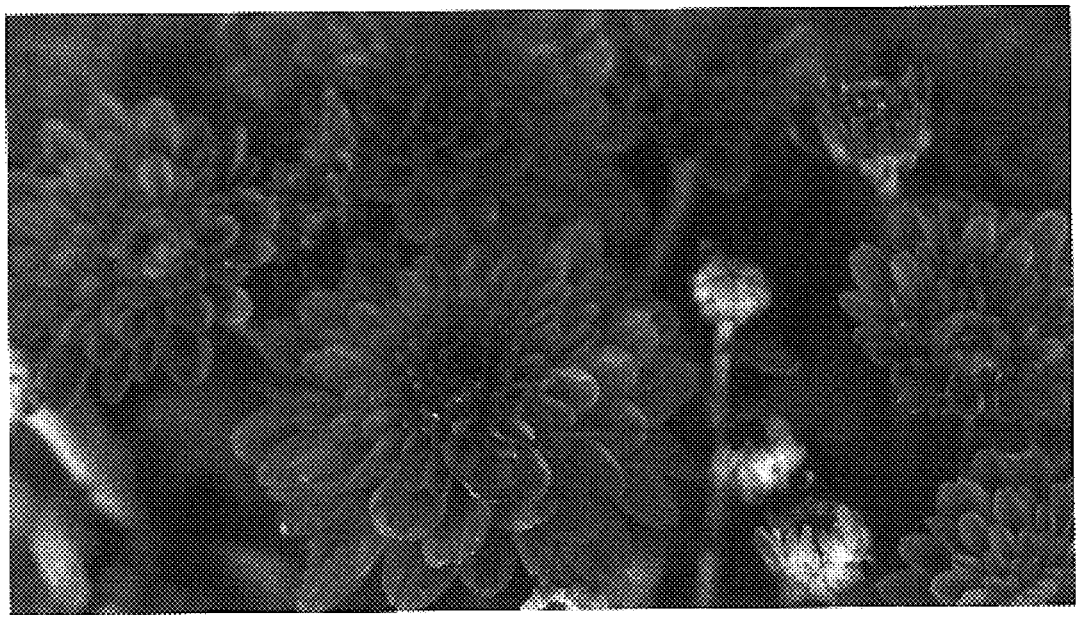

* * * * *